(12) United States Patent
Renslow

(10) Patent No.: US 7,850,919 B2
(45) Date of Patent: Dec. 14, 2010

(54) LIQUID SAMPLE COLLECTOR INTERFACE

(76) Inventor: Bruce Renslow, 3722 Agave Cir., Lancaster, CA (US) 93536-6264

( * ) Notice: Subject to any disclaimer, the term of this patent is extended or adjusted under 35 U.S.C. 154(b) by 227 days.

(21) Appl. No.: 12/072,644

(22) Filed: Feb. 27, 2008

(65) Prior Publication Data
US 2010/0202929 A1    Aug. 12, 2010

Related U.S. Application Data

(60) Provisional application No. 60/904,035, filed on Feb. 28, 2007.

(51) Int. Cl.
| B01L 3/00 | (2006.01) |
| B01L 99/00 | (2010.01) |
| A61M 5/00 | (2006.01) |
| B01D 27/00 | (2006.01) |
| B01D 35/00 | (2006.01) |
| B01D 35/28 | (2006.01) |
| G01N 1/22 | (2006.01) |
| A01N 1/00 | (2006.01) |

(52) U.S. Cl. .................... 422/99; 422/101; 604/190; 210/446; 73/863.23; 435/284.1

(58) Field of Classification Search .................. 422/99, 422/104
See application file for complete search history.

(56) References Cited

U.S. PATENT DOCUMENTS 2,857,913 A * 10/1958 Miskel ................ 604/190
3,933,652 A * 1/1976 Weichselbaum et al. .... 210/446
4,127,131 A * 11/1978 Vaillancourt ............... 604/190
4,594,902 A * 6/1986 Compton et al. ......... 73/863.23
5,352,410 A * 10/1994 Hansen et al. ............... 422/58
D377,152 S    1/1997 Renslow et al.
5,639,953 A    6/1997 Renslow
5,639,974 A    6/1997 Renslow
5,682,001 A   10/1997 Renslow
5,816,701 A   10/1998 Martin et al.
6,006,777 A   12/1999 Renslow
D424,458 S    5/2000 Renslow et al.
6,076,410 A    6/2000 Renslow
6,170,980 B1   1/2001 Martin
6,422,098 B1   7/2002 Renslow et al.
7,179,637 B2 * 2/2007 Feygin et al. ............ 435/284.1
7,588,732 B2 * 9/2009 Buss ......................... 422/101
2002/0119076 A1  8/2002 Dean et al.

OTHER PUBLICATIONS

Online definition—"Interlock," p. 1-3, 2010, <www.dictionary.com>.*

* cited by examiner

*Primary Examiner*—Jill Warden
*Assistant Examiner*—Bryan T Kilpatrick
(74) *Attorney, Agent, or Firm*—Patent Law Agency, LLC; Peter Ganjian

(57) ABSTRACT

Liquid sample collector interface, comprising a cap detachably interlocked with housing, with the cap having a filter chamber that accommodates a filter with a large surface area that extends beyond an end of the filter chamber for easy removal of the filter without the use of tools.

8 Claims, 14 Drawing Sheets

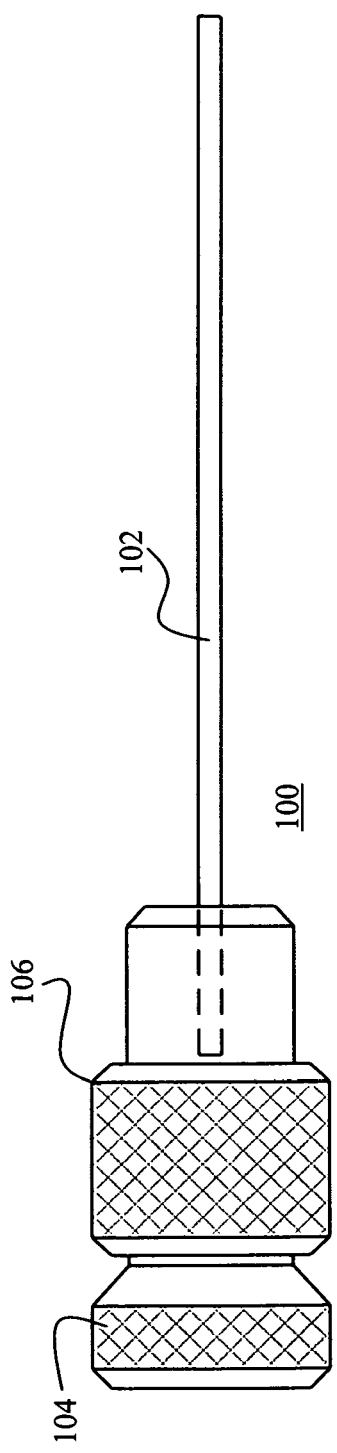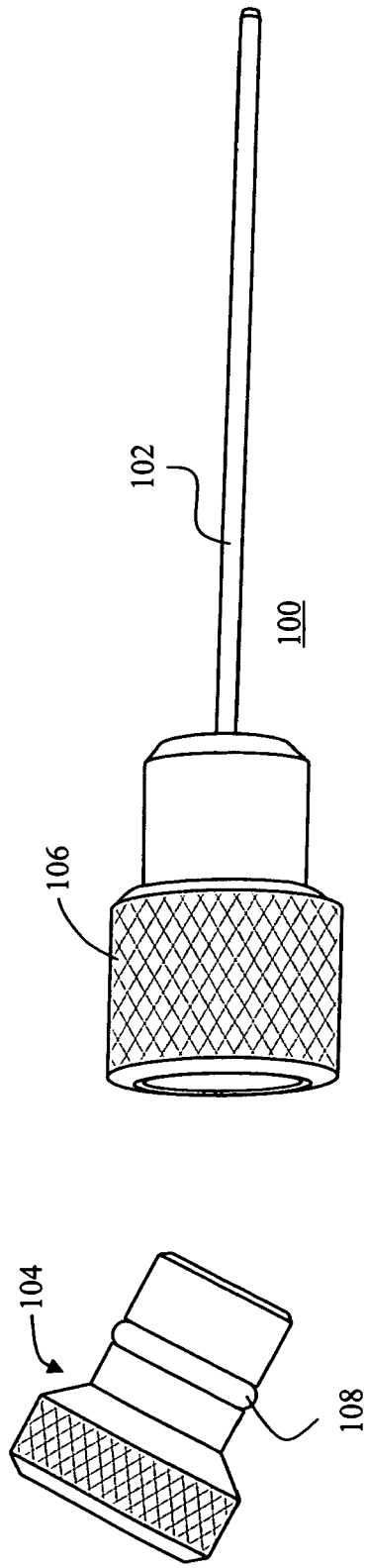
FIG. 1A (PRIOR ART)
FIG. 1B (PRIOR ART)

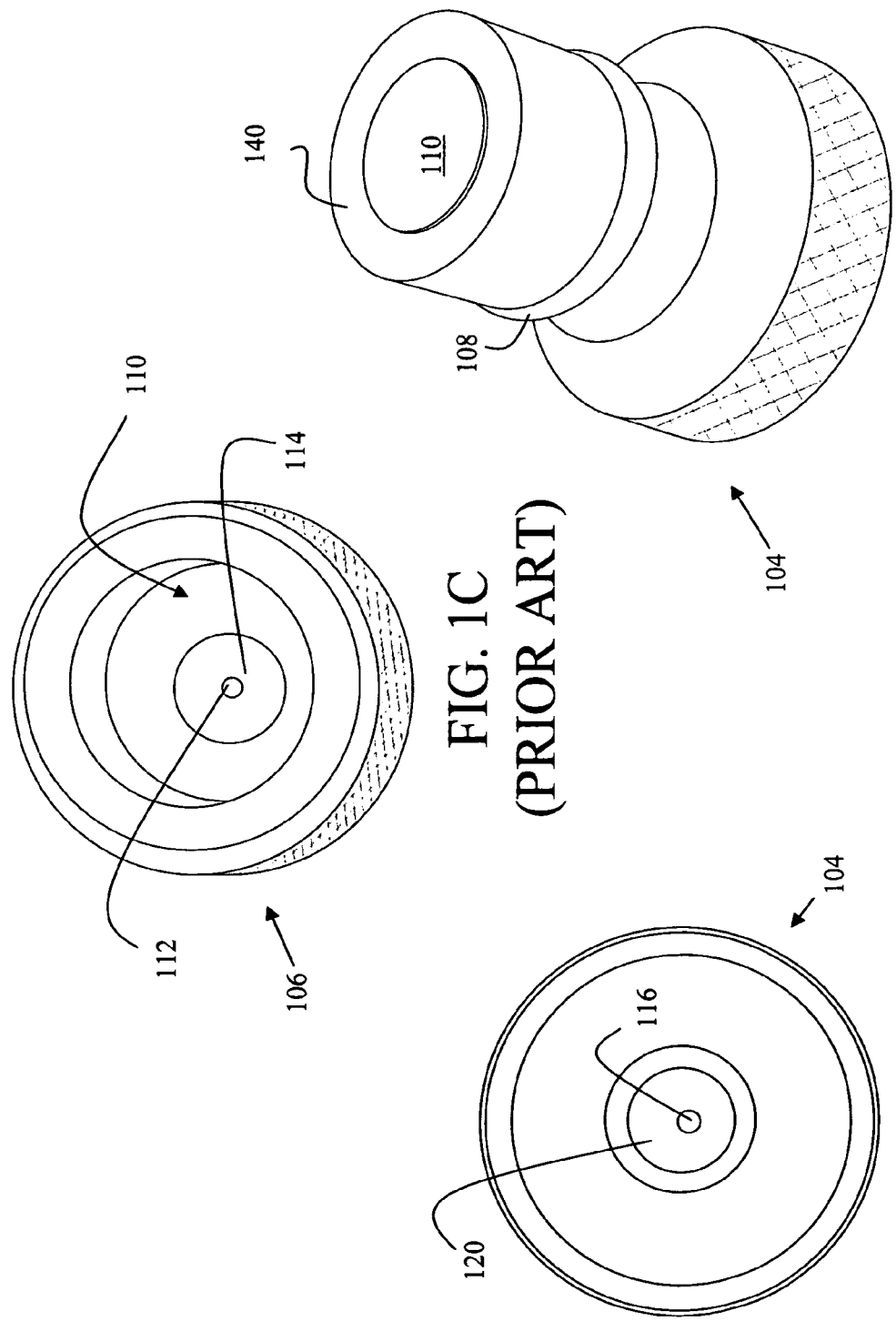

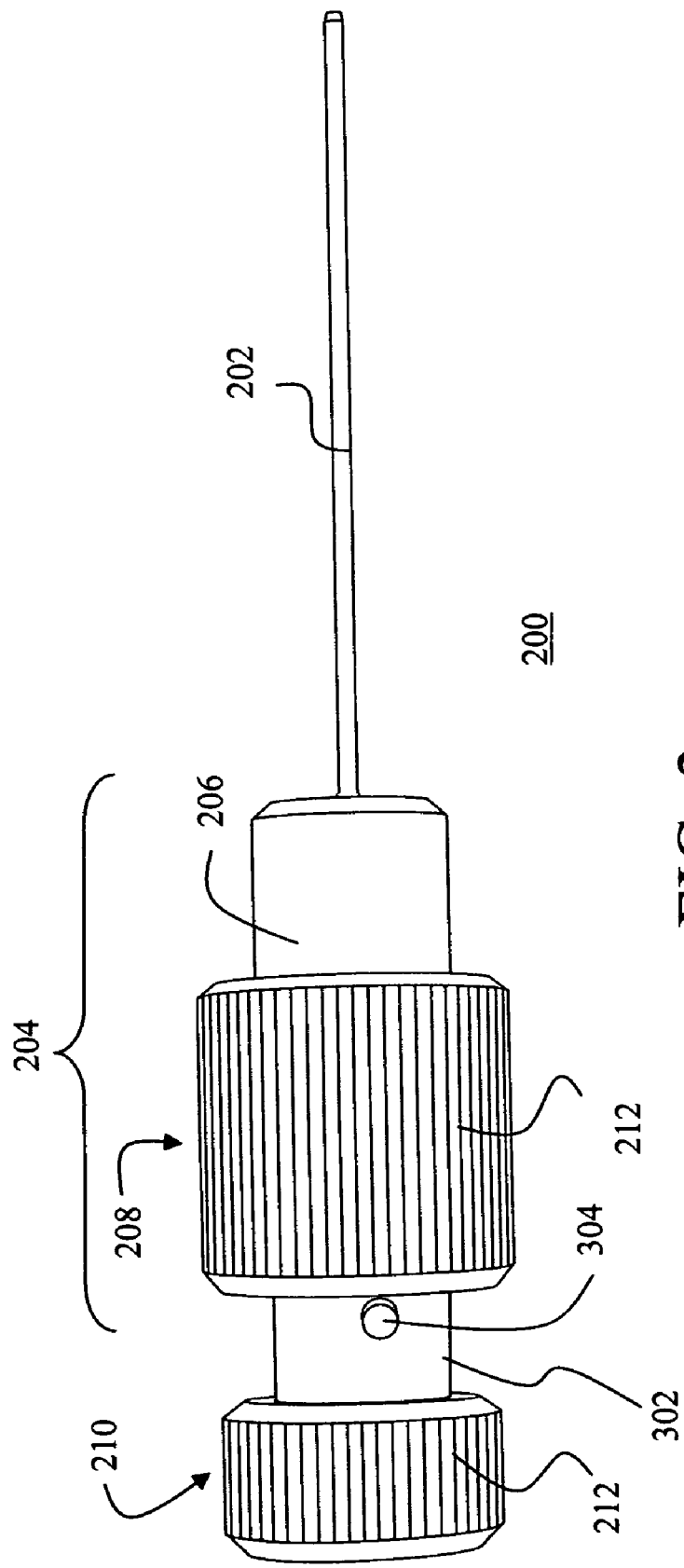

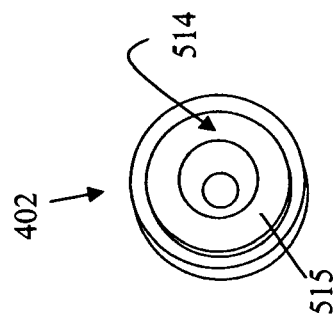
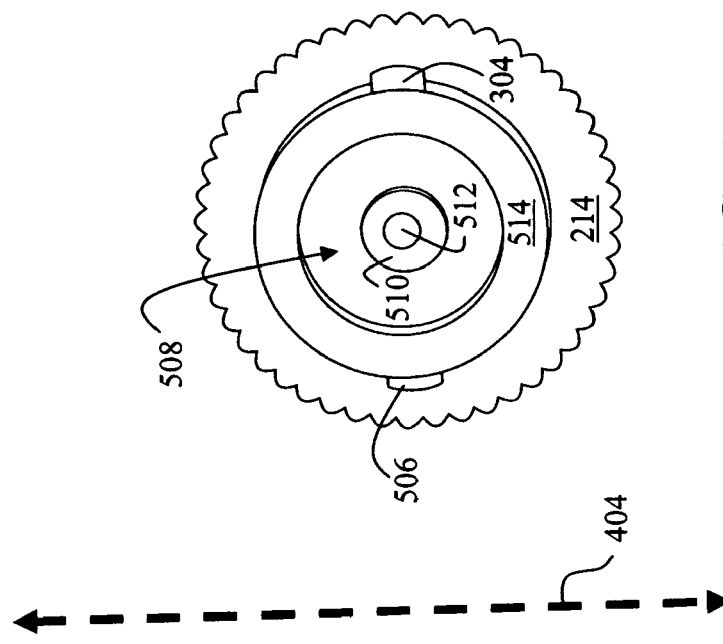
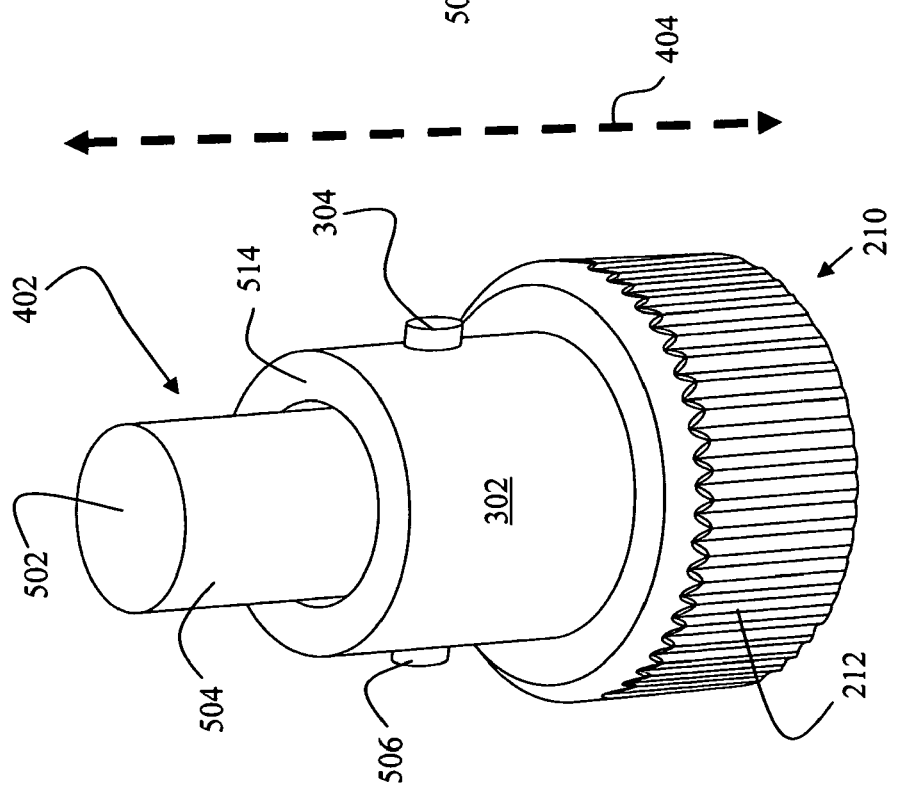

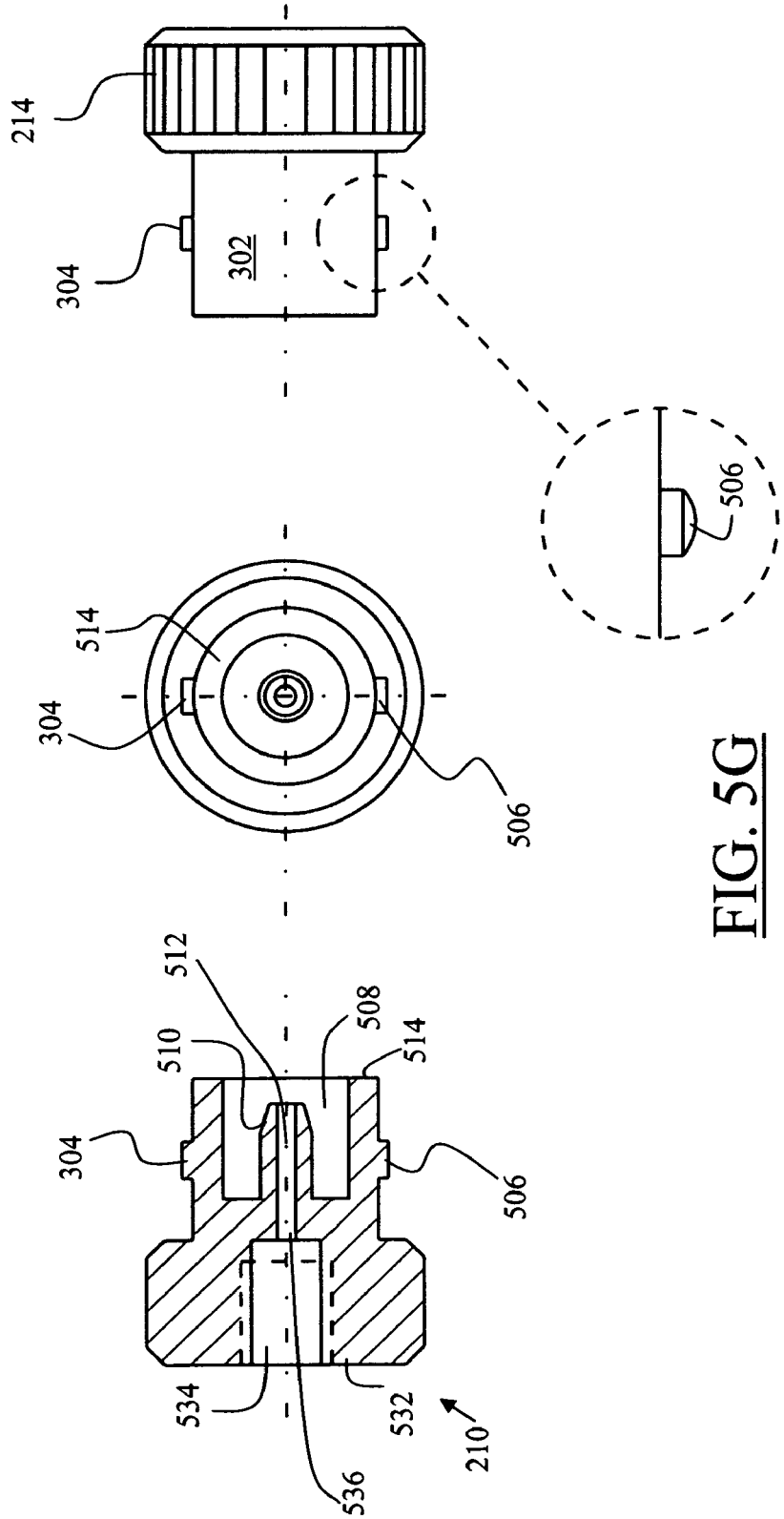

LIQUID SAMPLE COLLECTOR INTERFACE

CROSS-REFERENCE TO RELATED APPLICATIONS

This Application claims the benefit of priority of U.S. Utility Provisional Patent Application No. 60/904,035, filed 28 Feb. 2007, the entire disclosure of which is expressly incorporated by reference in its entirety herein.

BACKGROUND OF THE INVENTION

1. Field of the Invention

This invention relates to liquid sample collector interface used for collecting samples in dissolution testing apparatuses and, in particular, to liquid sample collector interface in the form of cannulas with high capacity filters and improved housing.

2. Description of Related Art

Drugs are commonly manufactured in the form of pills, which are disseminated into the body over a period as the pill dissolves. Manufacturers of pills are required by law to determine the precise dissolving characteristics of a pill before it is placed on the market. In the pharmaceutical industry, the stirring or agitation of sample drugs or other substances in test vessels is an important step in mimicking the dissolution rate or dissolution characteristics of a drug within the stomach. Examples of such test procedures include those performed for the purpose of testing and analyzing the rate at which doses of a drug is released from pharmaceutical products, such as tablets or capsules, under controlled conditions. The procedural steps, test duration, dissolution medium, and apparatus employed in dissolution tests typically must comply with established, well-recognized guidelines, such as those promulgated by United States Pharmacopeia (USP), in order for the test to be accepted as valid for the specific substance tested. The apparatus utilized for carrying out dissolution testing typically includes a vessel plate having an array of apertures into which test vessels are mounted.

Each test vessel includes a liquid called media, which is a dissolution bath that essentially duplicates the liquid solution that is contained within the stomach, with a precise quantity of the solution placed within the test vessel. The pill or capsule to be tested is then inserted within the test vessel with a mixing paddle inserted therein the test vessel to mix the solution at a precise rate, which duplicates the natural turbulence (churning) that is created within the stomach. Aliquots are then removed from the solution at precise time intervals, which are then analyzed to determine the amount of drug that has been dissolved within the solution in relation to the time that the pill or capsule has been in the solution.

In general, the removal of aliquots (dissolution samples) may be accomplished by cannulas of the type illustrated in the prior art FIG. 1A, which are known as resident cannulas. They are called resident cannulas because a stainless steel hypodermic tubing 102 portion of the resident cannula 100 resides within the media (dissolution bath) throughout a dissolution test period. As illustrated, the resident cannula 100 is comprised of the stainless steel hypodermic tubing 102, which is press fitted into an exterior of a housing 106 of the cannula 100. As best illustrated in FIG. 1B, the housing 106 includes an enclosure or cap 104 that has a cylindrical outer perimeter that frictional secures within the commensurately configured housing 106 by an O-ring washer 108, which also seals the cap 104 within the housing 106. As best illustrated in FIG. 1C, the housing 106 has a hallow cylindrical interior 110, with an aperture 112 that communicates with an end of the press-fitted stainless steel hypodermic tubing 102. As illustrated, the bottom surface of the interior 110 of the housing 106, surrounding the aperture 112 is concaved, creating a holding area 114 for the media drawn, which prevents a disc configured filter 110 from blocking the aperture 112 when the cap 104 is assembled and secured within the housing 106.

As illustrated in FIG. 1D to 1G, the cap 104 includes a port 120 at the exterior side of the cap 104 with an aperture 116. The port 120 is generally coupled to a collection mechanism such as a pump, with the pump creating a vacuum to draw aliquots (dissolution samples) from the media through the stainless steel hypodermic tubing 102, the aperture 112 of the housing 106, and then the cap 104 via filter 110, the aperture 116, and the port 120 for testing. As illustrated in FIG. 1E, the cap 104 includes the disc shaped filter 110 housed within a cylindrical filter chamber 118, with the filter 110 removing possible "debris" from the media prior to removal and analysis thereof.

Regrettably, most prior art cannulas 100 suffer from obvious disadvantages in that the prior art uses a small capacity disc filter element 110 that may clog prematurely after passing only a small sample volume. This is critical for methods that require multiple sample time points or large sample volumes that are often the case with UV analysis. In addition, automated sampling systems commonly require several milliliters of wash volume to eliminate carryover, which quickly clog the filters 110. Another obvious disadvantage is that the filter disc 110 is installed flush with the end 140 of the cap 104 (FIG. 1E) and can only be removed with a tool 122 as illustrated in FIG. 1F. A further obvious disadvantage of the prior art cannulas is that the original design incorporates the filter cap 104 that is retained by a friction fit O-ring 108. The friction fitting is not sufficiently strong to handle the high pressure that is likely to occur during back washing. That is, the cap 104 will most likely pop-out of the housing 106 during the process. Back washing is a desirable method of extending the life of the filter element 110. Most auto-sampling systems may be programmed to perform backwashing.

Reference is made to the following few exemplary U.S. Patent Publications, including U.S. Pat. Nos. 5,639,953; 5,639,974; 5,682,001; 5,816,701; 6,006,777; 6,076,410; 6,170,980; 6,422,098; D377,152; D424,458; 2002/0119076.

Accordingly, in light of the current state of the art and the drawbacks to current resident cannulas mentioned above, a need exists for a liquid sample collector interface that would use a filter with a larger surface area (higher capacity fitter), that the filter would be replaced without using any tools, and that would have a cap and housing coupling that would withstand back washing pressures.

BRIEF SUMMARY OF THE INVENTION

The present invention discloses a liquid sample collector interface comprising a cap that is detachably interlocked with a housing, with the cap having a filter chamber that accommodates a filter with a large surface area that extends beyond an end of the filter chamber for easy removal of the filter without the use of tools.

One aspect of the present invention provides a liquid sample collector interface, comprising a housing and a cap detachably interlocked with the housing for removably securing the cap onto the housing, which allows an assembled cap and housing to withstanding high back pressures encountered while backwashing. The cap has a filter chamber that accommodates a filter with a large surface area (high capacity) that extends beyond an end of the filter chamber for easy removal of the filter without the use of tools.

An optional aspect of the present invention provides a liquid sample collector interface, wherein the housing includes:
- a first groove oriented substantially vertically and substantially parallel along an axial length of the housing, formed within an inner perimeter of the housing chamber;
- a second groove oriented substantially vertically and substantially parallel along the axial length of the housing, and located diagonally opposite the first groove;
- a third groove oriented substantially horizontally and substantially perpendicular the axial length of the housing, and contiguous with the first groove;
- a fourth groove oriented substantially horizontally and substantially perpendicular the axial length of the housing, and contiguous with the second groove, with the third and forth grooves slanted towards a base of the housing at an angle; and
- an O-ring within a lower section of the housing, below the third and fourth groove, with a top edge of the filter chamber pressing against the O-ring, and providing a seal between the cap and the housing chamber;
- the base of the housing chamber is comprised of an aperture, and surrounding the aperture is concaved, creating a holding area, which prevents a closed end of a filter from blocking the aperture when the cap is assembled and secured within the housing.

Another optional aspect of the present invention provides a liquid sample collector interface, wherein:
- the cap includes a set of protuberances that are first moved along within the first and second grooves, and second within the third and fourth grooves to thereby interlock the cap with the housing.

Yet another optional aspect of the present invention provides a liquid sample collector interface, wherein:
- the slanting of the third and fourth grooves at the angle compels the set of protuberances interlocked within the grooves to tightly abut the cap with the housing.

A further optional aspect of the present invention provides a liquid sample collector interface, wherein:
- an exterior end of the housing includes one of a male thread connector, a female thread connector, and a press fitted cannula.

Still a further optional aspect of the present invention provide a liquid sample collector interface, wherein:
- the cap includes:
- the filter chamber that is comprised of a substantially cylindrical configuration having two protuberances on the outer perimeter of the filter chamber; and
- a port at an exterior end.

Another optional aspect of the present invention provides a liquid sample collector interface, wherein:
- the filter is comprised of a substantially cylindrical configuration, with a open end and a closed end;
- filter includes an interior cylindrical hollow section with gradually decreasing inner diameter from the open end towards the closed end;
- the filter is inserted via the open end into the filter chamber, and has a height along an axial length of the filter that is longer than a height of the filter chamber.

Yet another optional aspect of the present invention provides a liquid sample collector interface, wherein:
- filter chamber is comprised of a receptacle that is protruded from a center base of the filter chamber with an axial through hole, and is substantially cylindrical having a height that is less than the height of the filter chamber, with a gradually decreasing diameter from a free end towards the base of the filter chamber;
- the receptacle is inserted into the interior cylindrical hollow section of the filter, with the filter frictionally secured on the receptacle as the decreasing diameter of the filter from the open end towards the closed end increasing abuts the gradually increasing diameter of the receptacle from the free end towards the base.

These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" is used exclusively to mean "serving as an example, instance, or illustration." Any embodiment described as "exemplary" is not necessarily to be construed as preferred or advantageous over other embodiments.

Referring to the drawings in which like reference character(s) present corresponding part(s) throughout:

FIG. 1A is an exemplary illustration of a fully assembled prior art cannula;

FIG. 1B is an exemplary illustration of a disassembled prior art cannula shown in FIG. 1A;

FIG. 1C is an exemplary illustration of the housing chamber of the prior art cannula illustrated in FIG. 1A;

FIG. 1D is an exemplary illustration of the exterior side of the cap of the prior art cannula illustrated in FIG. 1A;

FIG. 1E is an exemplary illustration of the cap of the prior art cannula illustrated in FIG. 1A;

FIG. 3 is an exemplary side-view perspective illustration of a partially assembled liquid sample collector interface of FIG. 2;

FIGS. 5A to 5G are exemplary detailed illustrations of various views of a cap of the liquid sample collector interface illustrated in FIG. 2;

DETAILED DESCRIPTION OF THE INVENTION

The detailed description set forth below in connection with the appended drawings is intended as a description of presently preferred embodiments of the invention and is not intended to represent the only forms in which the present invention may be constructed and or utilized.

Figure 1G:
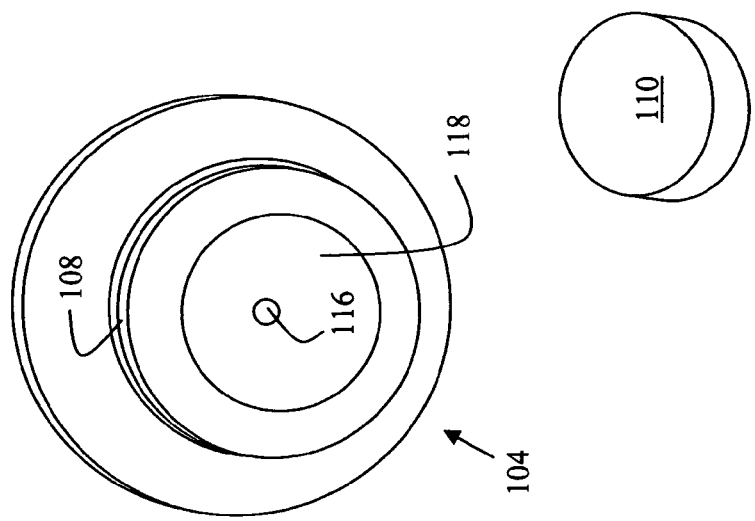
FIG. 1G is an exemplary illustration of the filter chamber of the cap of the prior art cannula-illustrated in FIG. 1A, including a prior art filter.
Figure 1F:
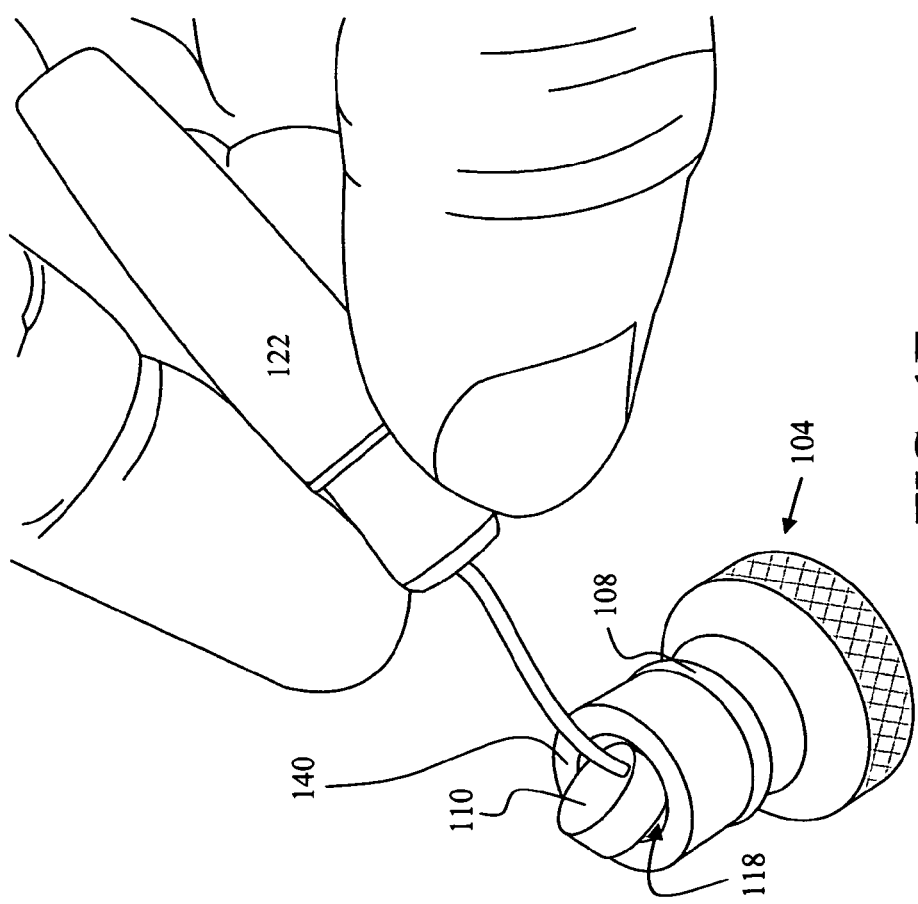
FIG. 1F is an exemplary illustration of an exemplary method of removal of a filter from the cap of the prior art cannula illustrated in FIG. 1A.
Figure 2:
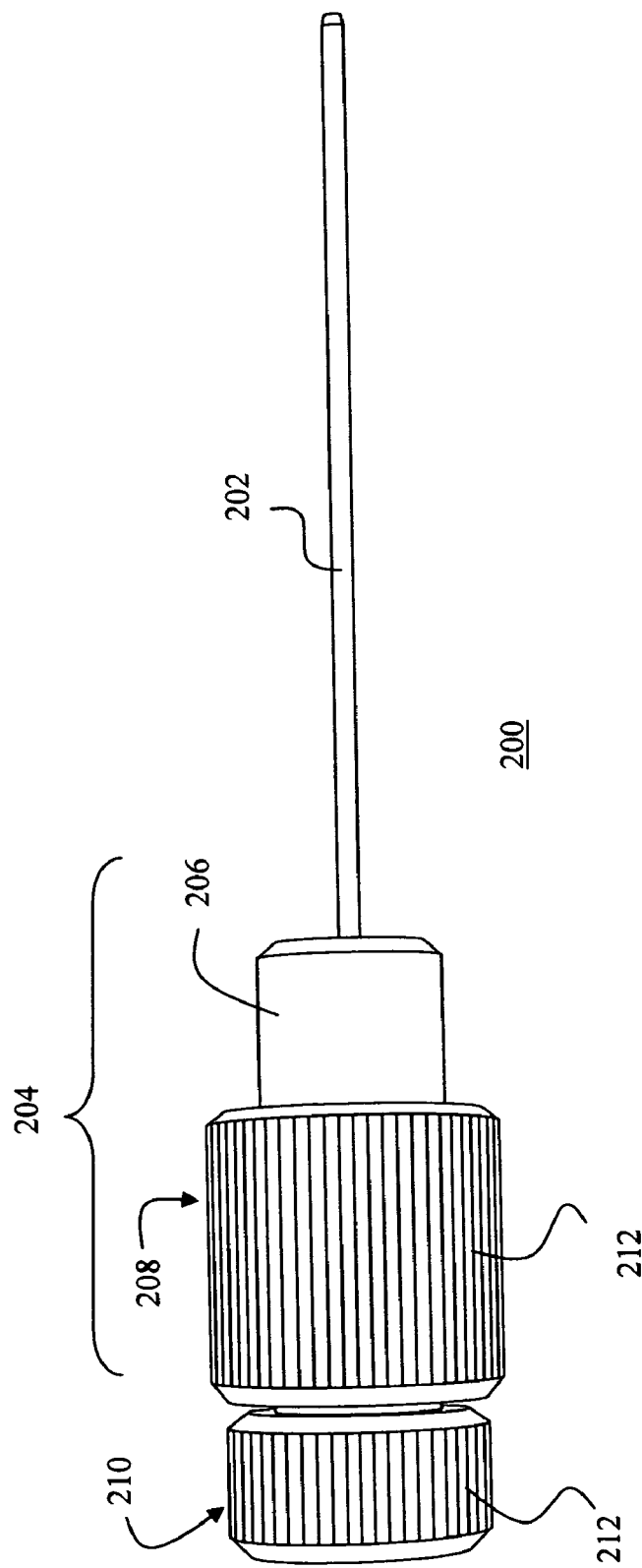
FIG. 2 is an exemplary side-view perspective illustration of a fully assembled liquid sample collector interface in accordance with the present invention.

FIG. 2 is an exemplary side-view perspective illustration of a fully assembled liquid sample collector interface in accordance with the present invention. As illustrated, the liquid sample collector interface 200 is comprised of a housing 204 that includes an exterior end (or head) 206 that accommodates a stainless steel hypodermic tubing 202, and a main housing body 208 with an exterior texture 212 that is striated, which facilitates for an ergonomic grip for assembling the liquid sample collector interface 200. Further included is a cap 210 with the exterior texture 212 that is also striated, detachably interlocked with the housing 204 for removably securing the cap 210 onto the housing 204, which allows an assembled cap 210 and housing 204 to withstanding high back pressures encountered while backwashing the liquid sample collector interface 200.

Figure 4A:
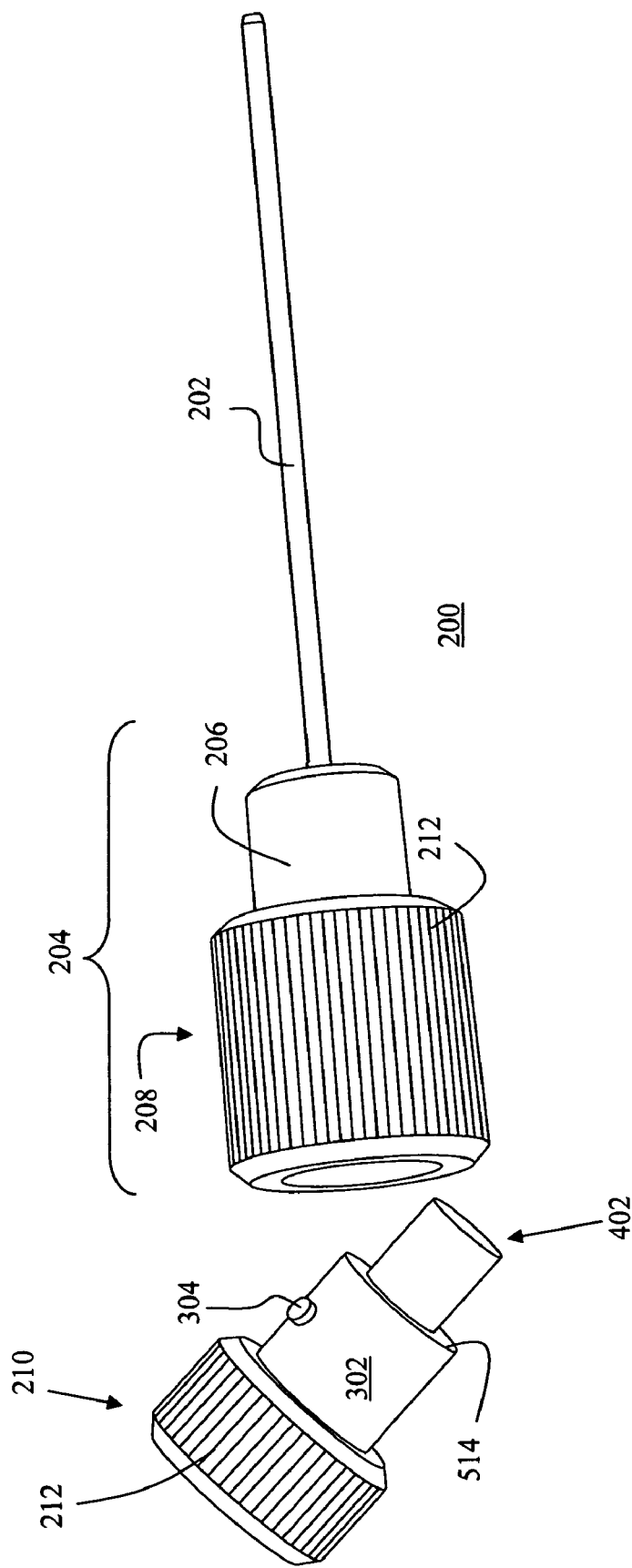
FIG. 4A is an exemplary perspective illustration of a disassembled liquid sample collector interface of FIG. 2.
Figure 4B:
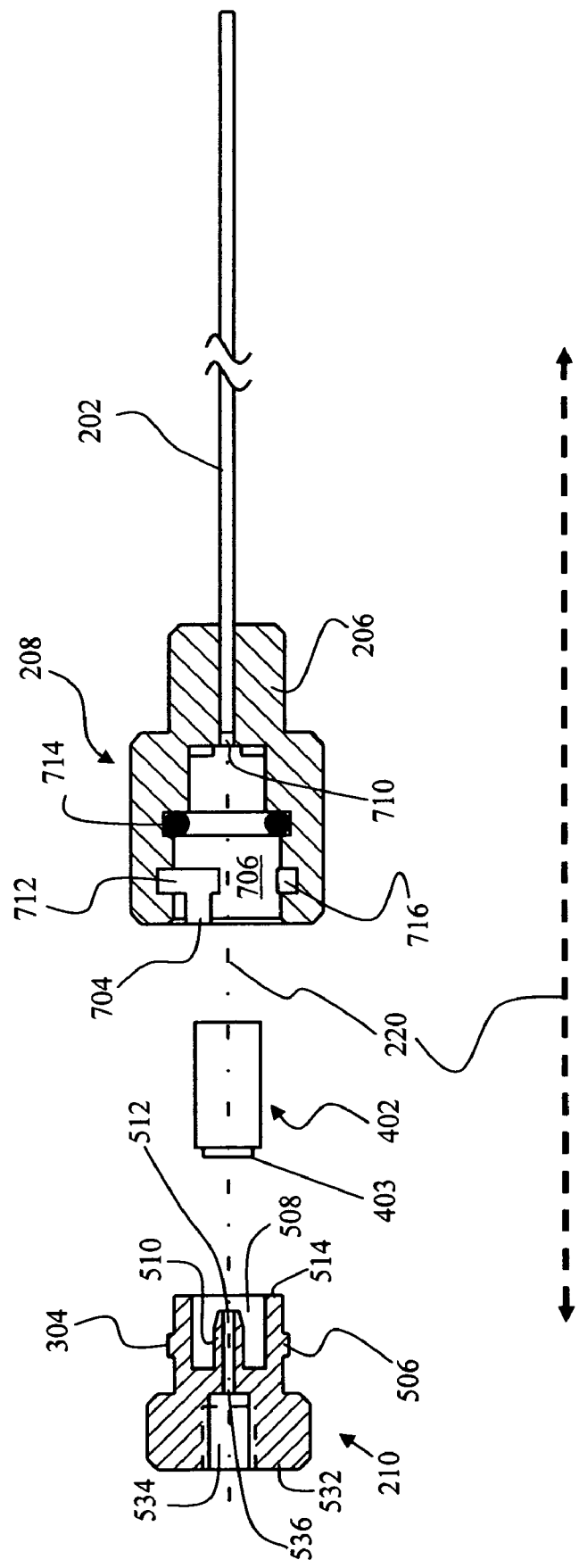
FIG. 4B is an exemplary cross-sectional illustration of the liquid sample collector interface of FIG. 2, along an axial length thereof.
Figure 5E:
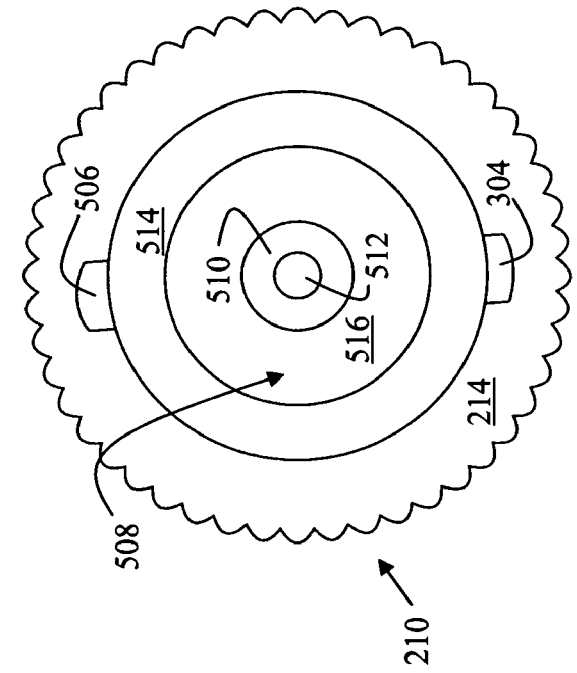
Figure 5F:
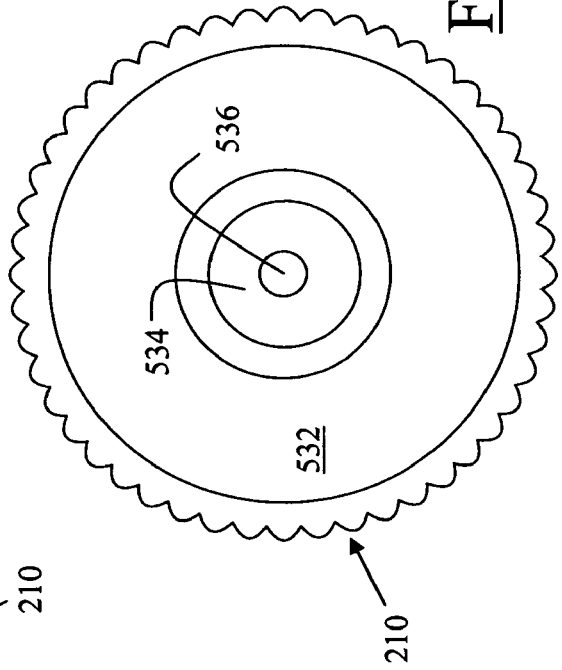
Figure 5D:
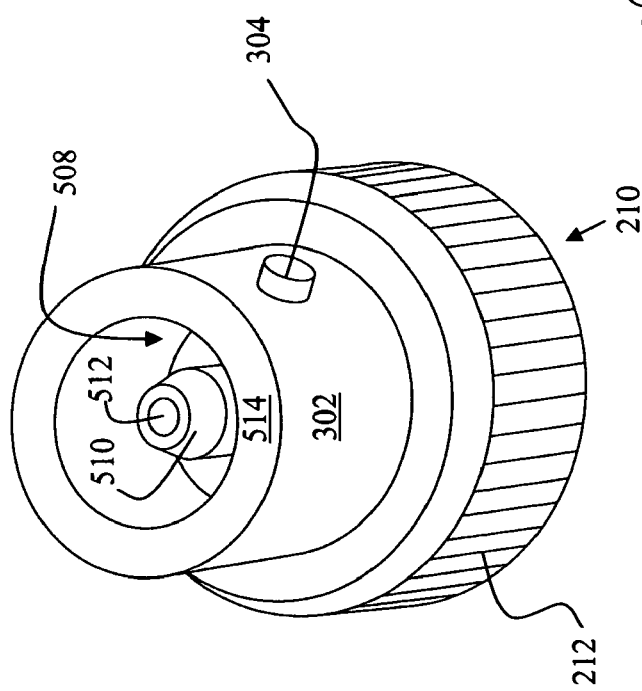
Figure 6B:
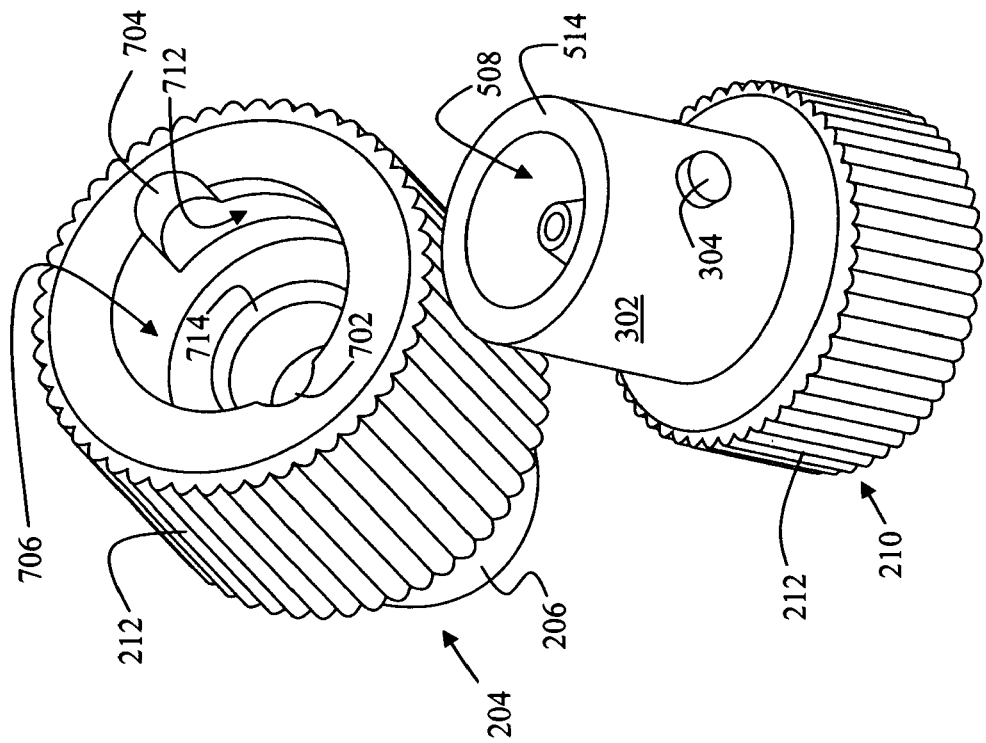
FIGS. 6A to 6E are exemplary detailed illustrations of various views of the housing juxtaposed with the cap of the liquid sample collector interface illustrated in FIG. 2.
Figure 6A:
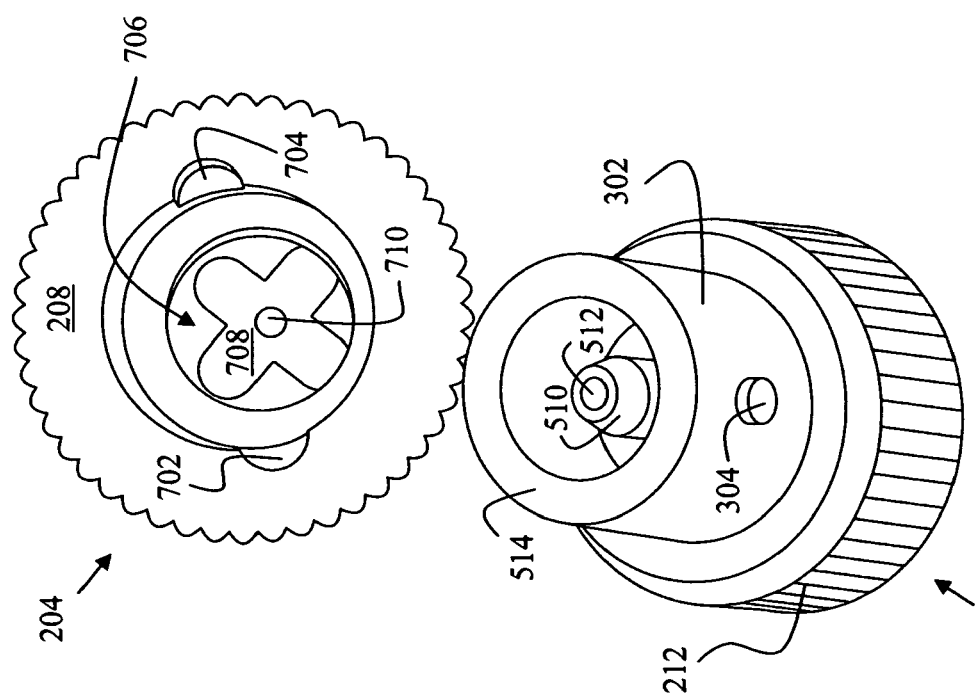
Figure 6D:
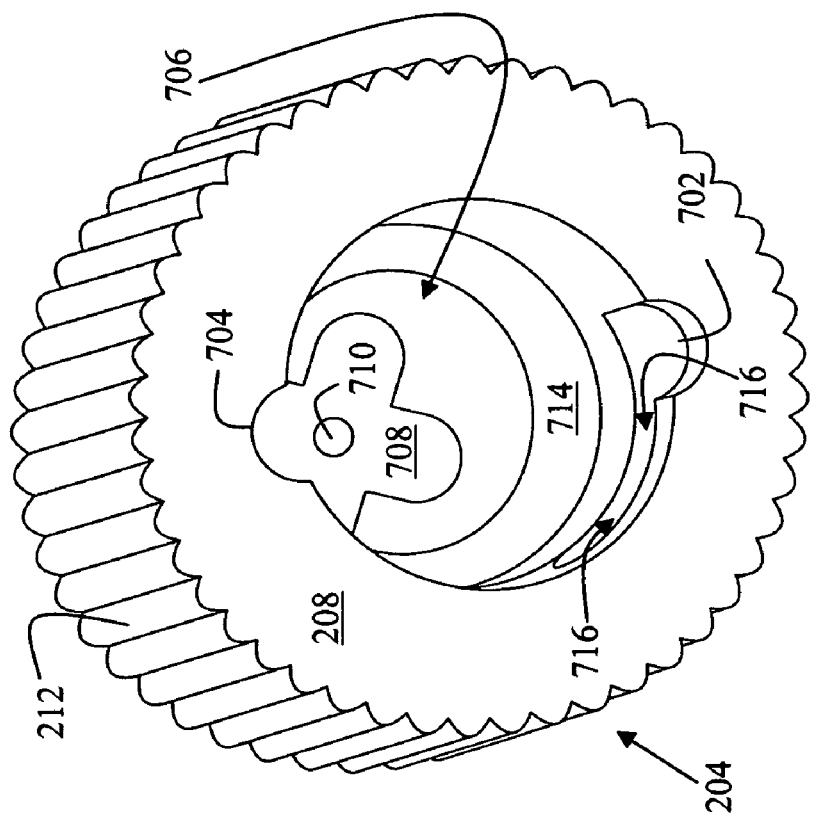
Figure 6C:
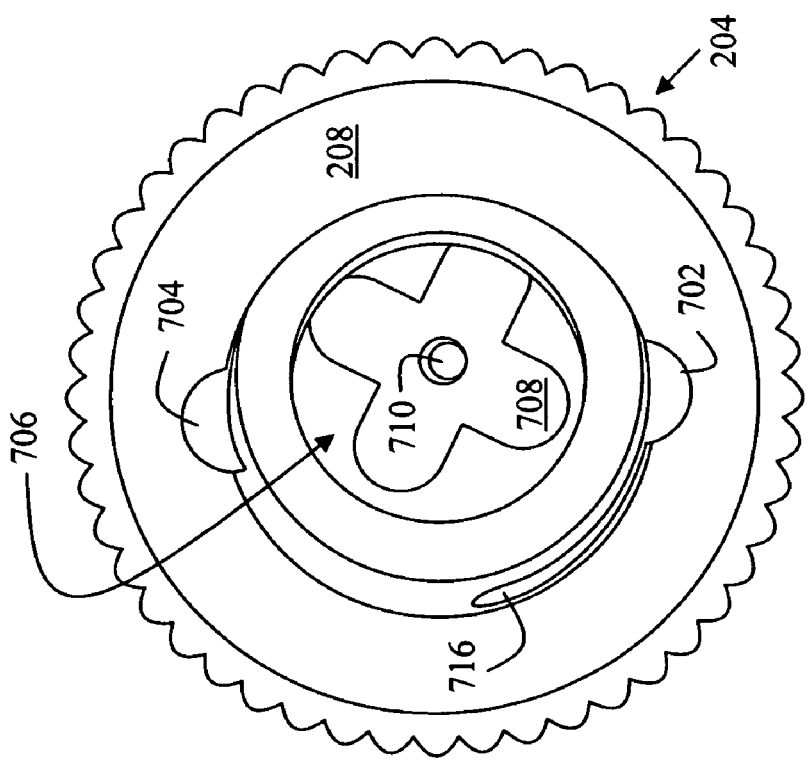
Figure 6E:
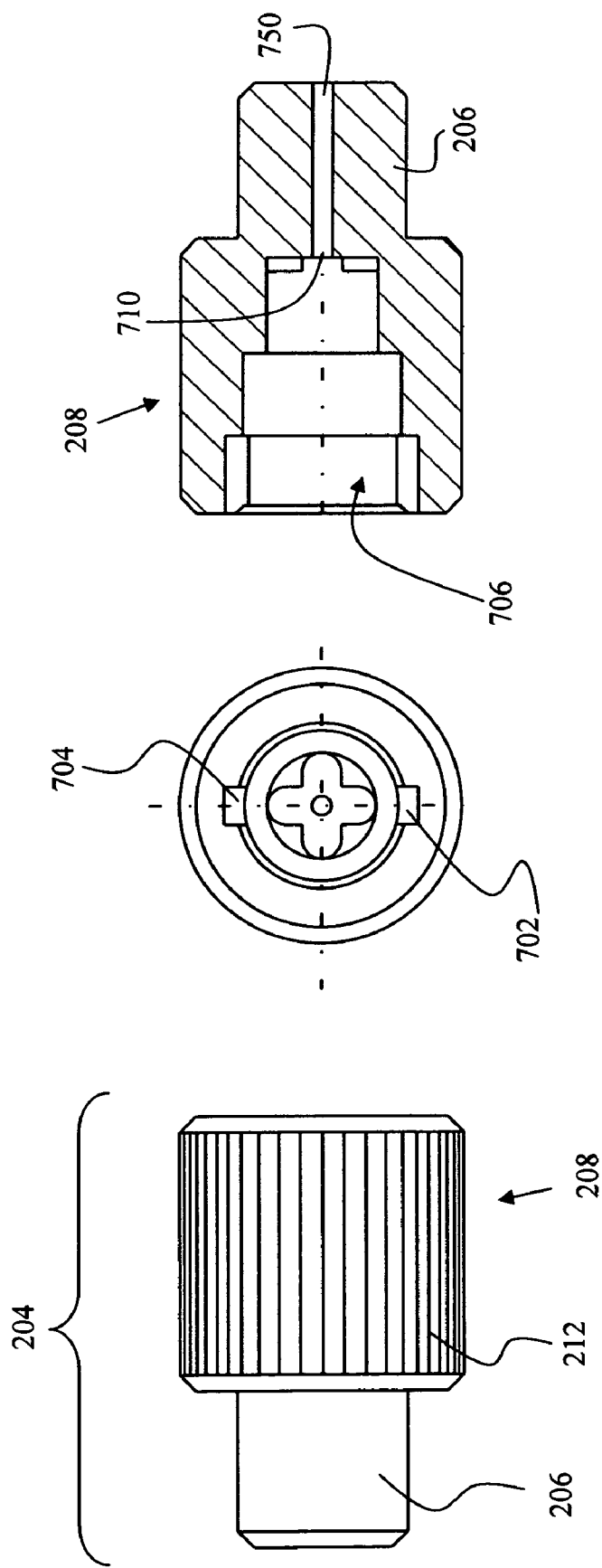

FIG. 3 is an exemplary side-view perspective illustration of a partially assembled liquid sample collector interface of FIG. 2. As illustrated, the cap 210 includes an axially extended cylinder 302 having a set of protuberances 304 and 506 (FIGS. 4B, 5A to 5G) that facilitate in interlocking the cap 210 with the housing 204. The axially extended cylinder 302 is inserted into housing 204 when fully assembled. As illustrated in FIG. 4A, which is an exemplary perspective illustration of a disassembled liquid sample collector interface of FIG. 2, the axially extended cylinder 302 forms the exterior wall of a filter chamber 508 (FIGS. 4B, 5A to 5G) that accommodates a filter 402. The filter 402 has a large surface area that extends axially beyond an end 514 of the axially extended cylinder 302 for easy removal of the filter 402 without the use of tools. The larger surface area of the filter 402 provides for a high capacity filter, which prevents premature clogging of the filter 402 after a short period of use. FIG. 4B is an exemplary cross-sectional illustration of the liquid sample collector interface 200 of FIG. 2, along an axial length 220 thereof. FIG. 4B is used as a convenient means to exemplarily illustrate most of the components of the liquid sample collector interface 200 in a single figure, the details of which are exemplarily illustrated in the remaining figures.

FIGS. 5A to 5G are exemplary detailed illustrations of various views of the cap of the liquid sample collector interface illustrated in FIG. 2. As illustrated in FIGS. 5A to 5G, the cap 210 includes a filter chamber 508 that is comprised of a substantially cylindrical configuration 302 having two protuberances 304 and 506 on the outer perimeter wall of the filter chamber 508. The filter 402 is a well-known filter that is comprised of a substantially cylindrical configuration, with an open end 514 and a closed end 502. The filter 402 includes an interior cylindrical hollow section 515 with gradually decreasing inner diameter from the open end 514 towards the closed end 502. The filter 402 is inserted via the open end 514 into the filter chamber 508, and has a height along an axial length of the filter 402 that is longer than a height of the filter chamber 508. That is, the height of the filter 402 extends beyond the edge 514 of the cap 210. This allows users to simply grab the closed end 502 of the filter 402 by hand, remove it, and replace it with a new filter without the use of any tools. As to the capacity of the filter 402, the larger surface area of this filter 402 is approximately 8 times the surface area of the prior art filter 110, which means that it has an approximate 8 times the capacity for filtration before the filter 402 is required to be replaced.

As further illustrated in FIGS. 5A to 5G, filter chamber 508 is comprised of a receptacle 510 that is protruded from a center base 516 of the filter chamber 508 with an axial through hole 512, and is substantially cylindrical having a height that is less than the height of the filter chamber 508, with a gradually decreasing diameter from a free end towards the base 516 of the filter chamber 508. The receptacle 510 is inserted into the interior cylindrical hollow section 515 of the filter 402, with the filter 402 frictionally secured on the receptacle 510 as the decreasing inner diameter of the filter 402 from the open end 514 towards the closed end 502 increasingly abuts the gradually increasing outer diameter of the receptacle 510 from the free end towards the base 516. The open end 514 of the filter 402 contacts the base 516 of the filter chamber 508. However, the tip of the receptacle 510 does not contact the closed interior portion of the filter 402. This is to prevent flow restriction. Accordingly, there is ample flow area within the filter 402 and in between the tip of the receptacle 510 and the closed interior end of the filter 402. Therefore, the through hole 512 of the receptacle 510 is aligned with an interior bottom center of the filter 402, but does not contact it, allowing for a free flow of aliquots without any restrictions. It should be noted that the small cylindrical protuberance 403 (FIG. 4B), which is the section of the filter 402 that contacts the base 516 of the filter chamber 508 is optional. As further illustrated in FIGS. 5A to 5G, the cap includes a port 534 at an exterior end 532 with an aperture 536. The port 534 is generally coupled to a collection mechanism such as a pump, with the pump creating a vacuum to draw aliquots (dissolution samples) from the media through the through hole 512 of the receptacle 510, and out of the aperture 536.

FIGS. 6A to 6E are exemplary detailed illustrations of various views of the housing juxtaposed with the cap of the liquid sample collector interface illustrated in FIG. 2. As illustrated in FIGS. 6A to 6E, the housing 204 includes a first groove 702 oriented substantially vertically and substantially parallel along an axial length of the housing 204, formed within an inner perimeter of the housing chamber 706. Further included is a second groove 704 oriented substantially vertically and substantially parallel along the axial length of the housing 204, and located diagonally opposite the first groove 702. The housing 204 further includes a third groove 716 oriented substantially horizontally and substantially perpendicular the axial length of the housing 204, and contiguous with the first groove 704. In addition, included is a fourth groove 712 oriented substantially horizontally and substantially perpendicular the axial length of the housing 204, and contiguous with the second groove 704, with the third 716 and forth 712 grooves slanted towards a base 708 of the housing 204 at an angle θ. As illustrated and described above, the cap 210 includes the set of protuberances 304 and 506 that interlock with the housing 204. The protuberances 304 and 506 are first moved along within the first and second grooves 702 and 704, and second within the third and fourth grooves 716 and 712 to thereby interlock the cap 210 with the housing 204. The slanting angle θ of the third and fourth grooves 716 and 712 compels the set of protuberances 304 and 506 interlocked within the grooves to tightly abut the cap 210 with the housing 204. That is, the slanted or sloped angle θ of the grooves 716 and 712 causes the cap 210 to be pulled in further into the chamber 706 of the housing 204, for a tighter interlocking.

As further illustrated, the housing also includes an O-ring 714 within a lower section of the housing chamber 706, below the third and fourth groove 716 and 712, with a top edge 514 of the filter chamber 508 pressing against the O-ring 714, which provides a seal between the cap 210 and the housing chamber 706 when the cap 210 and the housing 204 are interlocked. In general, the seal is required when pulling vacuum to pull out the media. Further, when backwashing, the seal prevents the content from being squirted out of the housing chamber 706. The base 708 of the housing is comprised of an aperture 710 with a concaved surrounding area, creating a holding area, which prevents the closed end of the filter 402 from blocking the aperture 710 when the cap 210 is assembled and secured within the housing 204.

Figure 7C:
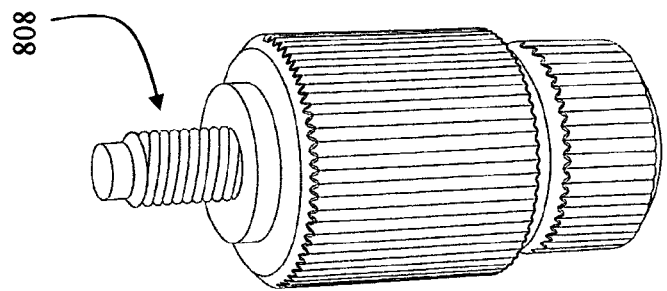
FIGS. 7A to 7C are exemplary illustrations of different embodiments of the liquid sample collector interface illustrated in FIG. 2 with varying heads in accordance with the present invention.
Figure 7B:
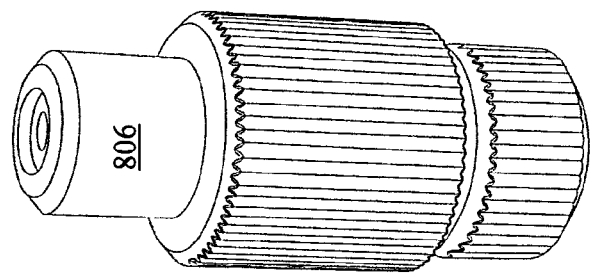
Figure 7A:
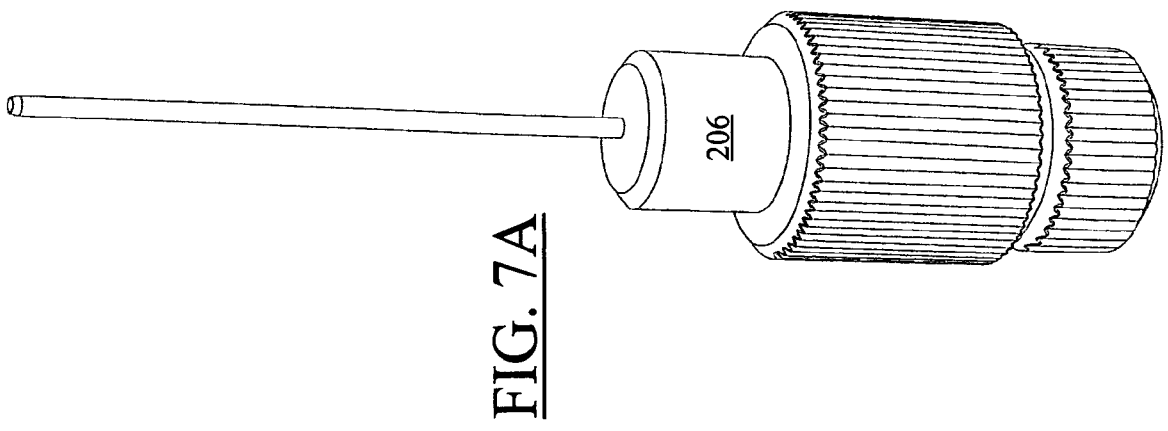

FIGS. 7A to 7C are exemplary illustrations of different embodiments of the liquid sample collector interface illustrated in FIG. 2 with varying heads in accordance with the present invention. As illustrated in FIGS. 7A to 7C, the exterior end of the housing 204 may include one of a press fitted cannula 206, a female thread connector 806, and male thread connector 808. A non-limiting exemplary application and use of the female threaded connector 806 and the male threaded connector 808 may include coupling the the two, with their respective ports coupled to other devices.

Although the invention has been described in considerable detail in language specific to structural features and or method acts, it is to be understood that the invention defined in the appended claims is not necessarily limited to the specific features or acts described. Rather, the specific features and acts are disclosed as preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. For example, other interlocking mechanism between the cap and the housing are possible, and should not be limited to the type illustrated and described. Such variations and alternate embodiments are contemplated, and can be made without departing from the spirit and scope of the invention.

It should further be noted that throughout the entire disclosure, the labels such as left, right, front, back top, bottom, forward, reverse, clockwise, counter clockwise, up, down, or other similar terms such as upper, lower, aft, fore, vertical, horizontal, proximal, distal, parallel, perpendicular, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. Liquid sample collector interface, comprising:
 a housing having a housing chamber for accommodating a portion of a filter;
 an exterior end of the housing includes one of a male thread connector, a female thread connector, and a press fitted cannula;
 a cap having a filter chamber that accommodates a remaining portion of the filter; with the filter having a large surface area that extends beyond an end of the filter chamber for easy removal of the filter without the use of tools;
 the cap detachably interlocks with the housing for removably securing the cap onto the housing, which allows an assembled cap and housing to fully accommodate the filter and withstanding high back pressures encountered while backwashing.

2. The liquid sample collector interface as set forth in claim 1, wherein:
 the housing includes:
 a first groove oriented substantially vertically and substantially parallel along an axial length of the housing, formed within an inner perimeter of the housing chamber;
 a second groove oriented substantially vertically and substantially parallel along the axial length of the housing, and located diagonally opposite the first groove;
 a third groove oriented substantially horizontally and substantially perpendicular the axial length of the housing, and contiguous with the first groove;
 a fourth groove oriented substantially horizontally and substantially perpendicular the axial length of the housing, and contiguous with the second groove, with the third and forth grooves slanted towards a base of the housing at an angle; and
 an O-ring within a lower section of the housing, below the third and fourth groove, with a top edge of the filter chamber pressing against the O-ring, and providing a seal between the cap and the housing chamber;
 the base of the housing chamber is comprised of an aperture, and surrounding the aperture is concaved, creating a holding area, which prevents a closed end of a filter from blocking the aperture when the cap is assembled and secured within the housing.

3. The liquid sample collector interface as set forth in claim 2, wherein:
 the cap includes a set of protuberances that are first moved along within the first and second grooves, and second within the third and fourth grooves to thereby interlock the cap with the housing.

4. The liquid sample collector interface as set forth in claim 3, wherein:
 the slanting of the third and fourth grooves at the angle compels the set of protuberances interlocked within the grooves to tightly abut the cap with the housing.

5. The liquid sample collector interface as set forth in claim 1, wherein:
 the cap includes:
 the filter chamber that is comprised of a substantially cylindrical configuration having two protuberances on the outer perimeter of the filter chamber; and a port at an exterior end.

6. The liquid sample collector interface as set forth in claim 1, wherein:
 the filter is comprised of a substantially cylindrical configuration, with a open end and a closed end;
 filter includes an interior cylindrical hollow section with gradually decreasing inner diameter from the open end towards the closed end;
 the filter is inserted via the open end into the filter chamber, and has a height along an axial length of the filter that is longer than a height of the filter chamber.

7. The liquid sample collector interface as set forth in claim 1, wherein:
 filter chamber is comprised of a receptacle that is protruded from a center base of the filter chamber with an axial through hole, and is substantially cylindrical having a height that is less than the height of the filter chamber, with a gradually decreasing diameter from a free end towards the base of the filter chamber;

the receptacle is inserted into the interior cylindrical hollow section of the filter, with the filter frictionally secured on the receptacle as the decreasing diameter of the filter from the open end towards the closed end increasing abuts the gradually increasing diameter of the receptacle from the free end towards the base.

8. A liquid sample collector interface, comprising:

a housing having a housing chamber for accommodating a portion of a filter;

an exterior end of the housing includes one of a male thread connector, a female thread connector, and a press fitted cannula;

a cap having a filter chamber that accommodates a remaining portion of the filter ; with the filter having a large surface area that extends beyond an end of the filter chamber for easy removal of the filter without the use of tools;

the cap detachably interlocks with the housing for removably securing the cap onto the housing, which allows an assembled cap and housing to fully accommodate the filter and withstanding high back pressures encountered while backwashing;

the filter chamber includes a substantially cylindrical configuration having two protuberances on the outer perimeter of the filter chamber.

* * * * *